United States Patent [19]

Padgett

[11] Patent Number: 4,644,586

[45] Date of Patent: Feb. 17, 1987

[54] COMBINATION STERILIZATION AND INFECTIOUS WASTE DISPOSAL CONTAINER

[75] Inventor: Lonnie W. Padgett, Acworth, Ga.

[73] Assignee: Kimberly-Clark Corporation, Neenah, Wis.

[21] Appl. No.: 664,463

[22] Filed: Oct. 25, 1984

[51] Int. Cl.$^4$ ............................................. B65D 33/01
[52] U.S. Cl. ................................... 383/102; 206/439; 206/484.1; 383/38; 383/88; 422/26
[58] Field of Search ................. 383/102, 88, 124, 38; 206/439, 440, 364, 365, 484.1; 422/26, 27, 34, 300, 310

[56] References Cited

U.S. PATENT DOCUMENTS

| | | | |
|---|---|---|---|
| 1,176,115 | 3/1916 | Way | 206/439 X |
| 2,333,587 | 11/1943 | Salfisburg | 383/88 X |
| 2,357,339 | 9/1944 | Mathieu | 383/38 X |
| 2,947,415 | 8/1960 | Garth | 206/364 |
| 3,016,284 | 1/1962 | Trexler | 383/102 X |
| 3,027,261 | 3/1962 | Sawara | 383/88 X |
| 3,728,839 | 4/1973 | Glick | 422/34 X |
| 3,761,013 | 9/1973 | Schuster | 206/439 |
| 4,041,203 | 8/1977 | Brock et al. | 428/157 |
| 4,057,144 | 11/1977 | Schuster | 206/439 |
| 4,091,922 | 5/1978 | Egler | 206/364 |
| 4,270,658 | 6/1981 | Schuster | 206/439 |
| 4,379,192 | 4/1983 | Wahlquist et al. | 428/156 |
| 4,380,485 | 4/1983 | Schuster | 156/254 |
| 4,482,053 | 11/1984 | Alpen et al. | 206/439 |

Primary Examiner—William Price
Assistant Examiner—Bryon Gehman
Attorney, Agent, or Firm—William D. Herrick

[57] ABSTRACT

A container particularly adapted to sterilize and use for disposal of contaminated or infectious waste in hospitals, industrial laboratories, and the like. One embodiment of the container is illustrated in the form of a bag constructed from a nonwoven web of thermoplastic fibers. The web is pervious to sterilants but impervious to bacteria and may comprise a laminate of webs of spunbonded and microfibers thermoplastic polymers. The container may be in the form of a bag and contains an impervious section which may be formed by coating or coextruding a polymer film and a pervious section comprising the nonwoven web. In addition to sealing at both ends, the container is capable of being sealed by means of heat, adhesives, or the like between the two sections. In a particularly useful application, infectious or contaminated waste is positioned within the pervious section and the impervious section folded underneath. This combination is subjected to sterilization conditions after which the contents are moved to the impervious section and the impervious section is sealed off thus enclosing the contents in a sealed pouch which may be handled or further disposed with minimum risk of contact with the contents. An alternative embodiment is in the form of a box having a panel with an aperture covered with pervious material and adapted to be sealed with an impervious barrier layer.

5 Claims, 8 Drawing Figures

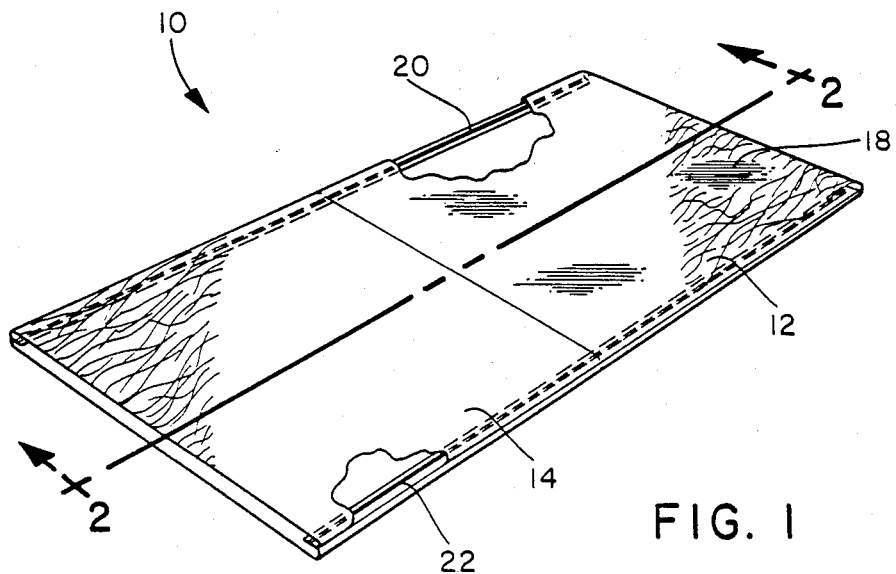
FIG. 1
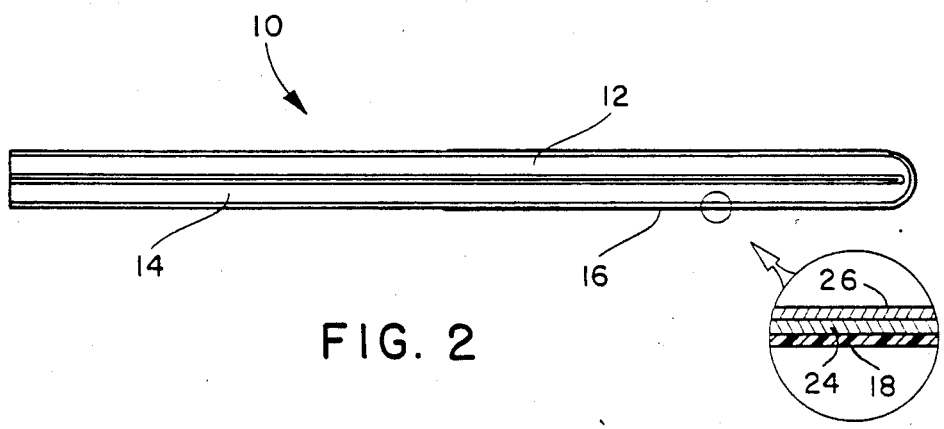
FIG. 2
FIG. 2A
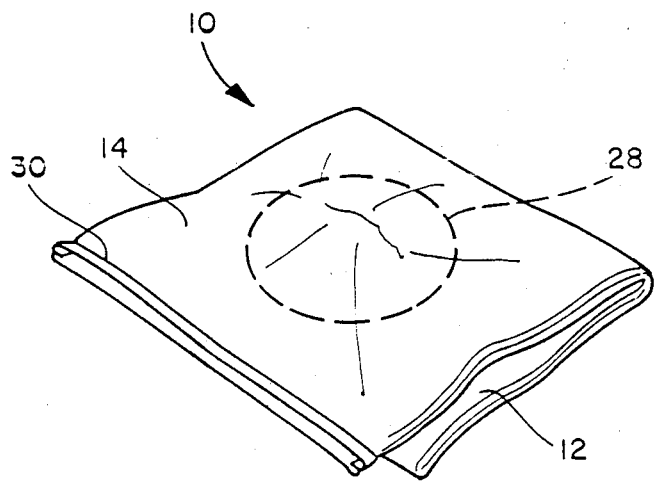
FIG. 3

COMBINATION STERILIZATION AND INFECTIOUS WASTE DISPOSAL CONTAINER

BACKGROUND OF THE INVENTION

1. Field of the Invention

The present invention relates to containers for items to be sterilized and also to containers for handling and disposing of contaminated or infectious waste products. Containers for items to be sterilized necessarily are porous to the sterilizing medium, whether steam or a gas such as ethylene oxide. On the other hand, such materials must be impervious to bacteria or other contaminants. Containers for contaminated or infectious waste products are desirably impervious to prevent exposure to the contaminated material. The present invention is directed to improvements in containers intended for such purposes and, in particular, to disposable containers such as bags or boxes that may advantageously be used for both applications.

2. Description of the Prior Art

Items to be sterilized are conventionally wrapped in muslin or nonwoven materials such as are described in U.S. Pat. No. 4,041,203 to Brock and Meitner dated Aug. 9, 1977, which is incorporated herein by reference. Once sterilized, however, if items are to be stored in a sterilized condition for extended periods, it is frequently considered desirable to further wrap the items in an impervious wrapper such as a film bag or the like. Such containers are described, for example, in U.S. Pat. No. 4,380,485 to Schuster dated Apr. 19, 1983 which includes as a material, a laminate of a barrier paper and a layer of thermoplastic polymer material having breather means. When it is desired to dispose of contaminated or infectious waste products, it may be desirable to sterilize such products prior to disposal. In such cases it has been considered necessary to use traditional sterilization containers for that purpose and transfer the sterilized waste into an impervious bag or container which is subsequently sealed prior to disposal. Such a procedure obviously presents a risk of contact with the waste material which, although subjected to sterilization, may not be completely decontaminated. Accordingly, such a procedure has not been entirely satisfactory, and it is desired to provide means for sterilization and also for handling infectious or contaminated waste with a minimized risk of contact.

SUMMARY OF THE INVENTION

The present invention is directed to improved containers particularly adapted to be used for sterilization purposes and also for containing and disposal of contaminated or infectious waste products. In particular, the present invention is directed to a single container that is useful for both purposes and minimizes the risk of contact with such contaminated or infectious waste. In one embodiment the container of the invention comprises a flexible nonwoven material that is continuous or seamed to be continuous and form first and second ends. Adjacent one of these ends the material is treated so as to be substantially impervious to liquids and gases, including moisture vapor while the section adjacent the other end is impervious to bacteria but pervious to sterilants such as steam or ethylene oxide. Means are provided to seal both of such ends and also to seal the container between the two sections. In preferred embodiments the container is formed from a nonwoven fabric containing thermoplastic fibers or filaments and the seals may then be formed by application of heat and pressure. In a particularly preferred embodiment the nonwoven fabric is a laminate of a spunbonded continuous filament web and a meltblown microfiber web such as is described in U.S. Pat. No. 4,041,203 to Brock and Meitner dated Aug. 9, 1977 which is coated with a polymer barrier film to form the impervious section.

In use to treat contaminated or infectious waste, the waste material is placed within the pervious section of the container, and the impervious section is folded underneath. This combination is placed, after sealing both ends, in a sterilant and sterilized. The container may then be lifted to cause the sterilized material to reposition itself into the impervious section, and the heat seal then formed between the two sections thus enclosing the sterilized contaminated material within a sealed pouch. In this manner, there is no need for contact with the contaminated or infectious material, and attendant risks are minimized.

In an alternative embodiment the container may be in the form of a box or other self-supporting structure of generally impervious material. In this embodiment one panel or wall of the structure will have an aperture that is covered by a flexible web such as the above-described laminate that is pervious to sterilants. In this case a barrier layer or film is associated with the structure and bonded thereto covering the flexible web when it is desired to seal the contents.

BRIEF DESCRIPTION OF THE DRAWINGS

FIG. 1 is a perspective view of a container in accordance with the invention in the form of a bag.

FIG. 2 illustrates the material from which the bag of FIG. 1 is made in cross section taken along lines 2—2 of FIG. 1.

FIG. 2A is an enlargement of the area defined by the circle in FIG. 2.

FIG. 3 illustrates the bag of FIG. 1 containing material to be sterilized and in folded condition.

DESCRIPTION OF THE PREFERRED EMBODIMENTS

Figure 4:
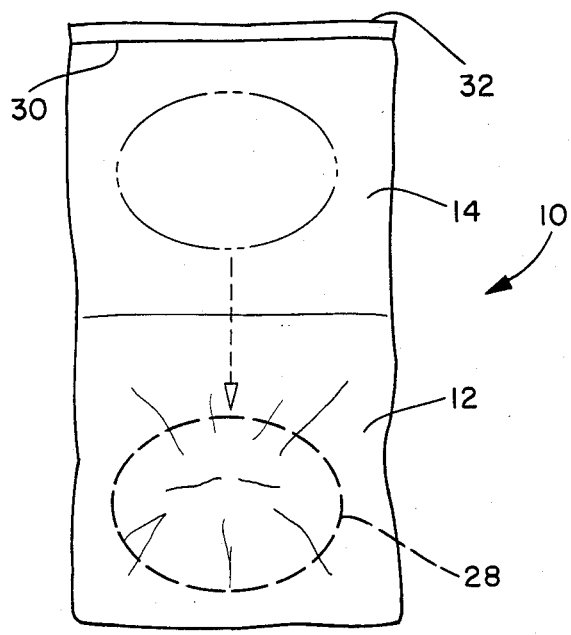
FIG. 4 illustrates the arrangement of FIG. 3 and the manner of repositioning the material into the impervious section.

The container of the invention is particularly suited for disposable applications. Accordingly, the container is preferably manufactured from nonwoven fabrics with a cost of manufacture consistent with disposability. Such fabrics will necessarily have properties dictated by the desired end use. In particular, for sterilization, the fabric must be penetratable by the sterliant to be used such as steam or water vapor, or gases such as ethylene oxide. On the other hand, it must also be impervious to bacteria to maintain sterility of the contents. In addition, since the container will be sealed for most applications, the nonwoven fabric must be capable of undergoing a sealing operation. While adhesives or other bonding means may be used for sealing, it is preferred that the nonwoven fabric be comprised of thermoplastic fibers or filaments and that it as well as the barrier or sealing layer be sealable by means of an application of heat and pressure. Taking into consideration these requirements, the preferred nonwoven fabric is that described in U.S. Pat. No. 4,041,203 to Brock and Meitner dated Aug. 9, 1977. This fabric comprises a laminate of meltblown thermoplastic polypropylene microfibers and a layer of spunbonded thermoplastic polypropylene filaments united by a patterned application of heat and pressure. While impervious to bacteria and many other contaminates, such material is pervious to sterilants, particularly gas sterilants such as ethylene oxide. Also such laminates may be readily heat sealed by further application of heat and pressure. For most applications a fabric basis weight in the range of from about 0.5 to 4.0 oz/yd$^2$ will be adequate and preferred embodiments will use a basis weight, for example, of about 1.0 to 2.5 oz/yd$^2$ for economy.

To obtain the desired impervious properties for the impervious section, it is preferred to apply to the nonwoven fabric a barrier coating or film of a thermoplastic polymer. Such films are known and may be applied, for example, by coextrusion or otherwise as described in U.S. Pat. No. 4,379,192 to Wahlquist and Schultz dated Apr. 5, 1983. Other means for obtaining the impervious properties may be employed such as manufacturing that section of the container to be sealed entirely from thermoplastic film or other impervious material. However, for ease of construction the coextrusion or coating step described is preferred. In general, this film will be effective at a thickness of about 1 to 2 mils so that the cost of thicker films will be avoided although they may be used if desired, for example, for reinforcement.

The size of the container will vary according to the intended use, and the relative sizes of the impervious and pervious sections may also be varied as will be apparent to those skilled in this art in view of the size of the intended contents. However, the respective sections will normally be about equal, especially for applications requiring transfer of sterilized material from one section to the other. Specialized applications such as for Mayo stand covers and the like may require varying configurations. In the carton embodiment, the size may vary widely as well, but the sterilant pervious portion will be of a size adequate to obtain sterilization within a satisfactory time without unduly weakening the structure as will be readily determined by those skilled in this art.

The preferred shape of the container is a bag form for ease of handling and application. The bag may be formed with the ends open or, if preferred, one end, generally the impervious section end, may be sealed. Any of the known bag forming operations may be employed, and the bag seams may be formed by conventional seam-forming steps such as adhesives, sonic bonding, application of heat and pressure, or the like. It is important, however, that the seams be constructed to maintain the pervious and impervious nature of the sections of the container. Examples of adhesives which may be used to form the seams include National Starch 34-2281 hot melt adhesive.

Turning to the figures, the invention will now be described in greater detail. FIG. 1 illustrates the container of the invention in perspective view. Specifically, container 10 comprises impervious section 12 and sterilant pervious section 14, both of which comprise nonwoven fabric 16. Impervious section 12, however, includes film coating 18 and the combined sections 12 and 14 are sealed along the edges by means of hot melt adhesive lines 20 and 22.

Turning to FIG. 2, the nonwoven fabric container construction will be described in further detail with reference to the cross section taken along lines 2—2 of FIG. 1. As shown in greater detail in FIG. 2A, fabric 16 is a laminate of spunbonded web 24 and meltblown web 26 to which is applied film 18 in the impervious section 12.

FIG. 3 illustrates the container of FIGS. 1 and 2 folded and in use for sterilization purposes. Thus, the material to be sterilized 28 is contained within pervious section 14 which is sealed by heat seal line 30. Impervious section 12 is folded beneath the material contained in pervious section 14 to present a neat bundle which may be conveniently handled. As shown, when subjected to sterilizing conditions, the sterilant may enter the container and sterilize the contents 28.

Turning to FIG. 4, there is shown the container of FIG. 3 repositioned to move contents 28 into the impervious section 12. This may be accomplished by simply lifting the container and contents by the end 32 of pervious section 13 whereby contents 28 will simply drop into impervious section 12.

Figure 5:
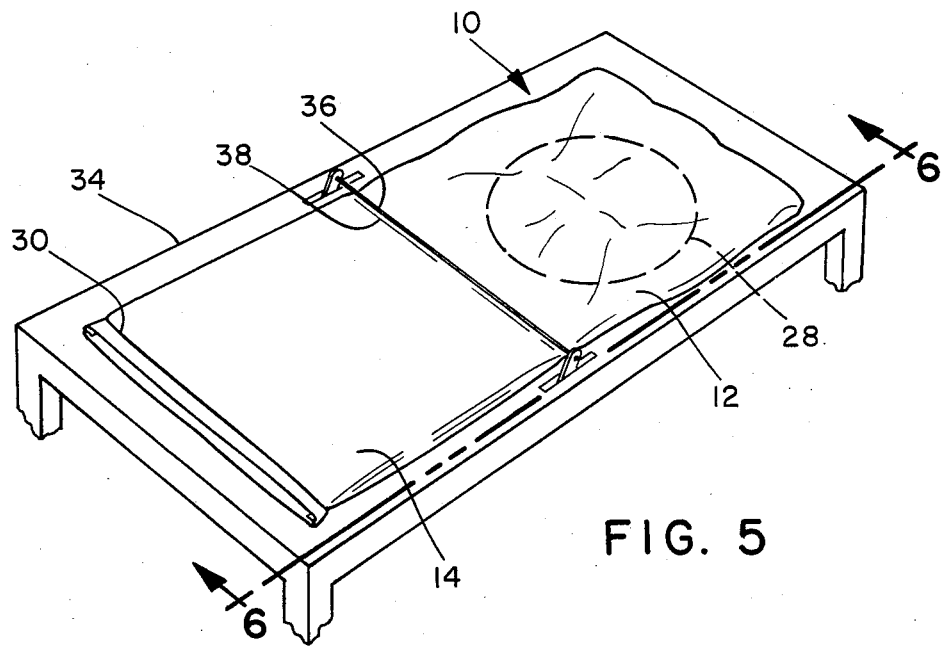
FIG. 5 illustrates the sealing of the container to enclose the material in a sealed pouch.
Figure 6:
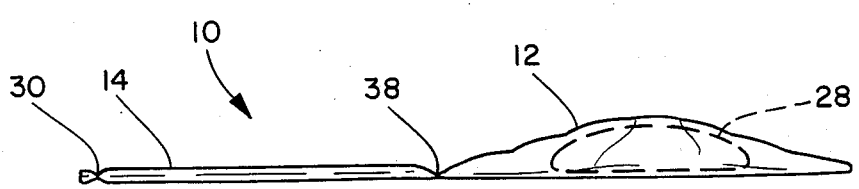
FIG. 6 is a side view of the sealed pouch of FIG. 5 viewed in the direction of arrows 6—6 to show the seal compartment.

FIG. 5 illustrates the container of FIG. 4 after this step has taken place and in position for sealing off of contents 28 in the impervious section 12. Thus, as illustrated, the container 10 and contents 28 may be positioned on a table 34 and hot wire 36 impressed on the container 10 in a region 38 between impervious section 12 and pervious section 14. Upon the application of this heat and pressure, the thermoplastic layers will be bonded to themselves sealing off contents 28 in a pouch formed by impervious section 12. This is further illustrated by means of FIG. 6 which is a side view of the container of FIG. 5 taken along lines 6—6. If desired, hot wire 36 can be used to simultaneously cut the thermoplastic layers removing pervious section 14.

Figure 7:
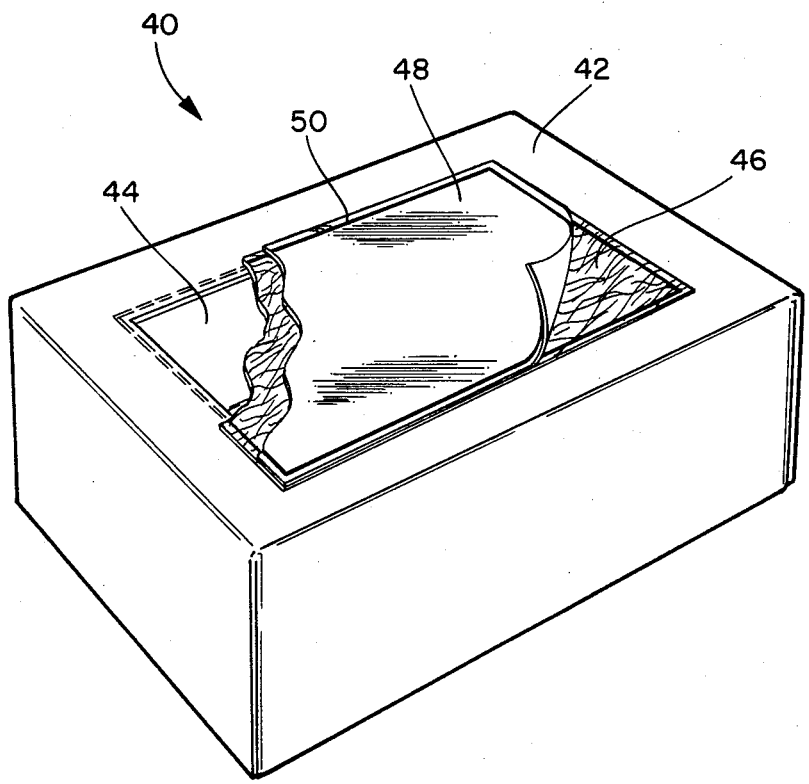
FIG. 7 is a perspective view of the container of the invention in the form of a box.

FIG. 7 illustrates the container of the invention in the form of box 40. This structure is formed from self-supporting material such as cardboard, corrugate, plastic or the like. At least one panel 42 will have an aperture 44 of sufficient size to admit sterilant and obtain sterilization within a desired time period. Covering this aperture is web 46 that may be any material permitting the sterilant to pass such as paper but is preferably the nonwoven laminate above described. Sealing is obtained by plastic layer 48 adapted to cover the web 46 and be sealed around the periphery by heat sealing or adhesives indicated at line 50. This embodiment finds application for disposal of large, bulky items such as animal cadavers which must be examined and sterilized prior to disposal in a sealed condition. Alternatively, it may be desired to ship the contents sealed and then remove the barrier layer to sterilize immediately prior to opening.

Thus, as shown, the container of the present invention presents the contaminated or infectious material in a completely sealed pouch which may then by handled for further disposal with a minimum risk. Moreover, the container of the invention will find many other applications for containing items to be sterilized such as Mayo stands, instruments, and the like. It can be seen that the particular advantages of the present invention lie in the economy of the construction which is consistent with disposability of the wide flexibility of the container for many and varied applications.

Thus is is apparent that there has been provided, in accordance with the invention, an improved container that fully satisfies the objects, aims, and advantages set forth above. While the invention has been described in conjunction with specific embodiments thereof, it is evident that many alternatives, modifications and variations will be apparent to those skilled in the art in light of the foregoing description. Accordingly, it is intended to embrace all such alternatives, modifications, and variations as fall within the spirit and broad scope of the appended claims.

I claim:

1. Container adapted to enclose material contents alternatively under conditions permitting sterilization or under sealed substantially gas and liquid impervious conditions comprising, first and second sections comprising a nonwoven thermoplastic flexible web that is pervious to sterilants but substantially impervious to bacteria, each of said first and second sections capable of completely enclosing said contents, a substantially vapor and liquid impermeable barrier film layer substantially completely covering the nonwoven web forming one of said first and second sections, said container being adapted to permit transfer of said contents from one of said first and second sections to the other and to seal between said first and second sections.

2. The container of claim 1 in the form of a bag and including a first end and a second end and a continuous sidewall between said first and second ends, and wherein means are provided for sealing both ends of said container.

3. The container of claim 2 wherein said flexible nonwoven fabric comprises thermoplastic fibers or filaments capable of forming said seals under conditions of heat and pressure.

4. The container of claim 3 wherein said nonwoven fabric comprises a laminate of a web of spunbonded filaments and a web of microfibers, and said laminate is coated with a film to form said impervious section.

5. The container of claim 4 wherein said nonwoven fabric comprises polypropylene filaments and microfibers.

* * * * *